United States Patent [19]

Beroza et al.

[11] 3,934,033
[45] Jan. 20, 1976

[54] METHOD FOR DISRUPTING NORMAL INSECT MATURATION

[75] Inventors: Morton Beroza, Silver Spring; Rafael Sarmiento, Laurel; Terrence P. McGovern, Bowie, all of Md.

[73] Assignee: The United States of America as represented by the Secretary of Agriculture, Washington, D.C.

[22] Filed: Nov. 26, 1974

[21] Appl. No.: 527,320

Related U.S. Application Data

[62] Division of Ser. No. 343,328, March 21, 1973, Pat. No. 3,873,724.

[52] U.S. Cl. ........ 424/341; 426/335; 424/DIG. 12
[51] Int. Cl.² ........................................... A01N 9/24

[58] Field of Search ...................... 44/341, DIG. 12

[56] References Cited
UNITED STATES PATENTS 3,711,519   1/1973   Dolejs et al. .................... 424/278

*Primary Examiner*—V. D. Turner
*Attorney, Agent, or Firm*—M. Howard Silverstein; William E. Scott

[57] ABSTRACT

7-Ethoxy-1-(p-ethylphenoxy)-3,7-dimethyl-2-octene and 1-(p-ethylphenoxy)-3,7-dimethyl-7-propoxy-2-octene are highly active in preventing normal maturation of the yellow mealworm and the confused flour beetle.

7 Claims, No Drawings

METHOD FOR DISRUPTING NORMAL INSECT MATURATION

A non-exclusive, irrevocable, royalty-free license in the invention herein described, throughout the world for all purposes of the United States Government, with the power to grant sublicenses for such purposes, is hereby granted to the Government of the United States of America.

This is a division, of application Ser. No. 343,328, filed Mar. 21, 1973, now U.S. Pat. No. 3,873,724.

This invention relates to a method and to compounds potentially useful for insect control, and more particularly to compounds having selective and high morphogenetic activity on certain insect species.

There is great need for insect-control chemicals that are safer and more selective in action than the broad-spectrum insecticides to make possible suppression of injurious insect populations without detrimental effects on nontarget species and the environment. Compounds mimicking juvenile hormones, that is, growth-regulating compounds found in insects, can be used to serve this purpose by upsetting the normal growth patterns of insects and thus preventing their normal maturation and reproduction.

Synthetic compounds exhibiting high juvenile hormone activity and related actions have been made. Among the most effective compounds are the aryl epoxyterpenoid ethers described by F. M. Pallos et al, Nature, 232, 486, 1971, by W. S. Bowers, Science, 164, 323, 1969. Tests of such compounds have shown promise for insect control in extensive tests which are still in progress. For further information see articles by R. W. Bagley and J. C. Bauernfield, pages 113–151, and F. M. Pallos and J. J. Menn, pages 303–316, in "Insect Juvenile Hormones, Chemistry and Action," J. J. Menn and M. Beroza, editors, Academic Press, New York, 1972.

An object of this invention is to provide novel compounds more potent than those currently available for the target species.

Another object of this invention is to produce compounds that are selective in action toward insects.

Another object is to provide compounds that are effective against injurious insects yet are not chemicals of a generally toxic type, that is, poisons, and therefore are not likely to be harmful if ingested in small amounts by human beings or by wildlife.

One other object is to provide inexpensive and effective materials for use in insect control.

According to our invention, two compounds, 7-ethoxy-1-(p-ethylphenoxy)-3,7,-dimethyl-2-octene and 1-(p-ethylphenoxy)-3,7-dimethyl-7-propoxy-2-octene, have been found to be exceptionally effective in preventing the normal development of the yellow mealworm and the confused flour beetle. Tests indicate the compounds are about 100 times as active against the yellow mealworm as the best compounds described by Pallos et al. and Bowers (loc. cit.).

For the synthesis of the two compounds the intermediate, 1-(p-ethylphenoxy)-3,7-dimethyl-2,6-octadiene, was prepared as described by R. E. Redfern et al., Journal of Economic Entomology, 64, 374–376 (1971). The procedure is essentially as follows: The sodium salt of p-ethylphenol was refluxed with geranyl bromide (1-bromo-3,7-dimethyl-2,6-octadiene) in ethanol for several hours to form the p-ethylphenyl geranyl ether which was worked up and distilled in the usual manner; b.p. 122–124/0.06 mm Hg.

The two compounds were prepared by alkoxymercuration of the above intermediate in the appropriate alcohol (ethanol or propanol) and demercuration of the reaction product with sodium borohydride. For example, 7-ethoxy-1-(p-ethylphenoxy)-3,7-dimethyl-2-octene was prepared as follows: A solution of mercuric acetate (0.01M) in 75 ml. ethanol was added during a 10-minute interval to a stirred, ice-cold solution of the intermediate described above (0.01M) in 30 ml. of ethanol. The ice bath was removed, and the reaction mixture was stirred for 30 minutes. A solution of potassium hydroxide (0.035 M) in 20 ml ethanol was added, and then aqueous sodium borohydride (0.005 M) was added in small portions. After stirring for 30 minutes, the solution was decanted from the mercury into water and the resulting mixture was extracted with ether several times. The combined ether extract was washed 3 times with water and once with saturated sodium chloride, and then dried over anhydrous magnesium sulfate. After removal of the solvent, the residue was chromatographed on a column of 75 grams of "Florisil" (a registered trademark for an activated magnesium silicate) activated 16 hours at 110°C. After 100 ml. hexane was percolated through the column, the compound was eluted with 2% ether in hexane. Fractions of this eluant containing the desired product (determined by gas chromatographic analysis) were combined. The product had the proper structure by NMR and infrared spectral analysis. For gas chromatographic analysis a 180-cm, 0.32-cm-o.d. stainless steel column containing 3% HI-EFF-8BP (cyclohexanedimethanol succinate) on 100/120 mesh Gas Chrom Q (silanized diatomaceous earth) was used with a column temperature of 185° and a nitrogen flow rate of 30 ml/min. Retention times were 10.2 and 12.2 minutes for the (Z) and (E) isomers, respectively. The product contained 75–80% of the (E) isomer in several preparations; $n_D^{25}$ = 1.5146.

The compound, 1-(p-ethylphenoxy)-3,7-dimethyl-7-propoxy-2-octene ($n_D^{25}$ = 1.4936) was also prepared by the above procedure except that propyl alcohol was used in place of ethanol. Using the aforementioned gas chromatographic column at 200° and a nitrogen flow rate of 30 ml/min the retention times were 5.35 and 6.40 minutes for the (Z) and (E) isomers, respectively. Since the basic intermediates used in the synthesis of the two compounds are not expensive, the compounds are potentially quite inexpensive.

In tests by topical application, activity of the compounds was determined by applying 1 μl of an acetone solution of each chemical topically to the venter of the last three abdominal segments of newly molted pupae (2 to 8 hours old) of the yellow mealworm, *Tenebrio molitor* L., and to last-instar nymphs of the large milkweed bug, *Oncopeltus fasciatus* (Dallas). Insects were held at room temperature (80°F., 50% R.H.) until the following molt to determine activity, which was signalled by retention of larval characteristics. Ten pupae were used for each dose of each compound. Responses of the yellow mealworm were rated 0 to 4 as follows: 0 = perfect adult, no activity; 1 = retention of gin traps or urogomphi; 2 = retention of gin traps and urogomphi; 3 = retention of gin traps and urogomphi and pupal cuticle retained around treatment area; 4 = second pupa — retention of all pupal characters. Responses were averaged for each chemical at each dose.

Tests of the two compounds prepared above and of related compounds against the yellow mealworm are summarized in Table I. In the first group of compounds in the Table (compounds No. 1-10), R' is ethyl and R is varied. In the second group of compounds (No. 2 and 11-14), R is ethyl and R' is varied. Although most of the compounds exhibit excellent activity, the activities of compounds No. 2 and 12 are outstanding and exceptional.

In contrast, when the compounds of Table 1 were applied to last instar nymphs of the large milkweed bug, they were comparatively ineffective. This difference in action demonstrates the high selectivity of action of these chemicals. This specificity can conceivably be utilized to combat an injurious insect species while allowing a beneficial one to survive unharmed.

Among other related compounds that were prepared and tested against the yellow mealworm are 7-ethoxy-3-ethyl-1-(p-ethylphenoxy)-7-methyl-2-octene and 7-ethoxy-1-(p-ethylphenoxy)-3,7-dimethyl-2-nonene; they were considerably less effective than compounds No. 2 and 12.

In a side-by-side test on the yellow mealworm of compound No. 2 of Table 1 and the best juvenile hormone mimic described by Pallos et al (loc. cit), 6,7-epoxy-1-(p-ethylphenoxy)-3,7-dimethyl-2-octene called Compound IV, compound No. 2 was about 100 times more active than their Compound IV.

We also tested compound No. 2 against another coleopteron, the confused flour beetle, *Tribolium confusum* Jacquelin duVal, by a different route of administration. In one test, last-instar larvae (20/jar) were placed in jars containing different concentrations of the chemical in 10 grams of 80-mesh bleached flour. With as little as 0.1 ppm of chemical in the flour, no adults were found after 4 weeks; with 0.05 ppm in the flour, five adults survived after 46 days, but their eggs failed to hatch. In contrast, 13 adults and 75 larvae per jar were present in the control (no chemical) after 46 days. In another test, eggs of the confused flour beetle (20/cup) were placed in ⅝-oz jelly cups each containing 5 grams 80-mesh bleached flour. With as little as 0.1 ppm of compound No. 2 in the flour, no adults were observed; with 0.02 ppm, two adults were noted after 47 days, but they produced no eggs. In similar tests with pupae and adults, 50 ppm of compound no. 2 did not prevent reproduction. Thus, the chemical is most effective when administered before the insects reach the pupal stage. Concentrations up to 50 ppm of compound no. 2 in the flour were tested; although minimum amounts to protect the flour are stated above the amount of chemical needed will depend on the length of time it is necessary to protect the flour.

In light of current knowledge, the two effective chemicals, compounds 2 and 12 in Table I, are likely to be useful against other Coleoptera in addition to the two species mentioned, that is, against insects of the same order. In addition, as has been demonstrated with other juvenile hormone mimics the chemicals may be administered by other routes such as by fumigation or dipping as well as by topical application or incorporation in food; the chemicals may be effective at different life stages of the insect depending on the species; they may be useful in breaking diapause; and, they may be formulated with other materials such as synergists or antioxidants to increase or prolong their action.

Table 1

Juvenile-hormone activity against the yellow mealworm of compounds having the formula

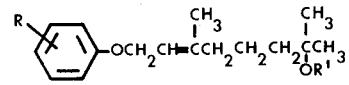

| Compound No. | R | R' | 10 | 1 | 0.1 | 0.01 | 0.001 | 0.0001 | 0.00001 | 0.000001 |
|---|---|---|---|---|---|---|---|---|---|---|
| 1 | p—CH₃ | C₂H₅ | 4.0 | 4.0 | 4.0 | 2.6 | 1.5 | | | |
| 2 | p—C₂H₅ | C₂H₅ | 4.0 | 4.0 | 4.0 | 4.0 | 3.3 | 2.1 | 1.8 | 1.1 |
| 3 | p—C₃H₇ | C₂H₅ | 4.0 | 4.0 | 4.0 | 2.5 | 2.0 | | | |
| 4 | p—CH(CH₃)₂ | C₂H₅ | 4.0 | 4.0 | 3.0 | 1.8 | | | | |
| 5 | p—OC₂H₅ | C₂H₅ | 4.0 | 4.0 | 4.0 | 2.3 | 1.0 | | | |
| 6 | 3,4-OCH₂O— | C₂H₅ | 4.0 | 4.0 | 4.0 | 3.0 | 0.5 | | | |
| 7 | m—Cl | C₂H₅ | 3.0 | 3.0 | 2.4 | 0.2 | | | | |
| 8 | p—Cl | C₂H₅ | 4.0 | 4.0 | 4.0 | 2.8 | 0.0 | | | |
| 9 | 3,4-diCl | C₂H₅ | 4.0 | 2.8 | 1.2 | | | | | |
| 10 | p—NO₂ | C₂H₅ | 4.0 | 4.0 | 3.7 | 1.2 | | | | |
| 11 | p—C₂H₅ | CH₃ | 4.0 | 4.0 | 2.4 | 0.0 | | | | |
| 2 | p—C₂H₅ | C₂H₅ | 4.0 | 4.0 | 4.0 | 4.0 | 3.3 | 2.1 | 1.8 | 1.1 |
| 12 | p—C₂H₅ | C₃H₇ | 4.0 | 4.0 | 4.0 | 4.0 | 4.0 | 2.7 | 1.7 | |
| 13 | p—C₂H₅ | C₄H₉ | 4.0 | 4.0 | 4.0 | 2.2 | 1.2 | | | |
| 14 | p—C₂H₅ | CH₂CH(CH₃)₂ | 4.0 | 3.8 | 4.0 | 3.0 | 1.6 | | | |

We claim:

1. A method of protecting flour from insects selected from the group consisting of the yellow mealworm, *Tenebrio molitor* (L.) and the confused flour beetle, *Tribolium confusum* Jacquelin duVal comprising incorporating into said flour an effective maturation inhibiting amount of a compound selected from the group consisting of 7-ethoxy-1-(p-ethylphenoxy)-3,7-dimethyl-2-octene and 1-(p-ethylphenoxy)-3,7-dimethyl-7-propoxy-2-octene.

2. The method of claim 1 wherein the insect is the yellow mealworm, *Tenebrio molitor* (L.).

3. The method of claim 2 wherein the compound is 7-ethoxy-1-(p-ethylphenoxy)-3,7-dimethyl-2-octene.

4. The method of claim 2 wherein the compound is 1-(p-ethylphenoxy)-3,7-dimethyl-7-propoxy-2-octene.

5. The method of claim 1 wherein the insect is the confused flour beetle, *Tribolium confusum* Jacqueline duVal.

6. The method of claim 5 wherein the compound is 7-ethoxy-1-(p-ethylphenoxy)-3,7-dimethyl-2-octene.

7. The method of claim 5 wherein the compound is 1-(p-ethylphenoxy)-3,7-dimethyl-7-propoxy-2-octene.

* * * * *

UNITED STATES PATENT OFFICE
CERTIFICATE OF CORRECTION

PATENT NO. : 3,934,033
DATED : January 20, 1976
INVENTOR(S) : Morton Beroza, Rafael Sarmiento, Terrence P. McGovern and Robert E. Redfern It is certified that error appears in the above-identified patent and that said Letters Patent are hereby corrected as shown below:

[75] Inventors: Morton Beroza, Silver Spring;
Rafael Sarmiento, Laurel; Terrence
P. McGovern, Bowie; and Robert E.
Redfern, Laurel, all of Md.

Signed and Sealed this

Twentieth Day of July 1976

[SEAL]

Attest:

RUTH C. MASON
Attesting Officer

C. MARSHALL DANN
Commissioner of Patents and Trademarks